(12) United States Patent
Bartels et al.

(10) Patent No.: US 8,923,986 B2
(45) Date of Patent: Dec. 30, 2014

(54) IMPLANTABLE MEDICAL LEAD

(75) Inventors: Klaus Bartels, Berlin (DE); Gernot Kolberg, Berlin (DE); Jochen Palm, Mahlow (DE)

(73) Assignee: Biotronik SE & Co. KG, Berlin (DE)

( * ) Notice: Subject to any disclaimer, the term of this patent is extended or adjusted under 35 U.S.C. 154(b) by 362 days.

(21) Appl. No.: 13/453,023

(22) Filed: Apr. 23, 2012

(65) Prior Publication Data

US 2012/0290056 A1 Nov. 15, 2012

Related U.S. Application Data

(60) Provisional application No. 61/484,239, filed on May 10, 2011.

(51) Int. Cl.
*A61N 1/05* (2006.01)
*H01R 3/00* (2006.01)
*A61N 1/08* (2006.01)

(52) U.S. Cl.
CPC ............. *A61N 1/05* (2013.01); *A61N 2001/086* (2013.01)
USPC ............................................ 607/116; 29/854

(58) Field of Classification Search
USPC ............................................ 607/116; 29/854
See application file for complete search history.

(56) References Cited

U.S. PATENT DOCUMENTS

| 2008/0154348 A1 | 6/2008 | Atalar et al. |
| 2008/0243218 A1 | 10/2008 | Bottomley et al. |
| 2010/0217262 A1 | 8/2010 | Stevenson et al. |

FOREIGN PATENT DOCUMENTS

| EP | 1872825 | 1/2008 |
| EP | 2465573 | 6/2012 |

OTHER PUBLICATIONS

European Search Report and Notes to the European Search Report on European Patent Application No. 12 16 4371, dated Sep. 18, 2012 (8 pages).

*Primary Examiner* — Mark W Bockelman
(74) *Attorney, Agent, or Firm* — Buchanan Ingersoll & Rooney PC

(57) ABSTRACT

An implantable medical lead for transmitting electrical pulses to excitable bodily tissue and/or signals detected at bodily tissue to a detection and evaluation unit, including a distal electrode or a distal sensor, or actuator; a proximal electrode connector or sensor/actuator connector; and a lead pole which connects the electrode or the sensor or actuator to the electrode connector or sensor/actuator connector and extends in the lead body, wherein the lead pole comprises at least two separate and individually insulated conductors which are electrically interconnected at least at one point which functions as an interchange point, or reversal point, in the lead extension from the proximal electrode or sensor connector to the distal electrode or the distal sensor, and wherein at least one of the separate conductors, in particular close to the reversal point, is interrupted at least once and/or is not connected at one end.

19 Claims, 8 Drawing Sheets

IMPLANTABLE MEDICAL LEAD

RELATED APPLICATION

This patent application claims the benefit of co-pending U.S. Provisional Patent Application No. 61/484,239, filed on May 10, 2011, which is hereby incorporated by reference in its entirety.

TECHNICAL FIELD

The present inventive disclosure relates to an implantable medical lead for transmitting electrical pulses to excitable bodily tissue and/or signals detected at bodily tissue to a detection and evaluation unit, comprising a distal electrode or a distal sensor or actuator, a proximal electrode connector or sensor/actuator connector, and a lead pole which connects the electrode or the sensor/actuator to the electrode connector or sensor/actuator connector and extends in the lead body. These are electrode leads in particular, although they can also be connecting lines of sensor systems or measuring systems for intracorporeal use, for example.

BACKGROUND

Medical implants such as, for example, pacemakers and defibrillators often include an electrical connection to the inside of the patient's body. A connection of this type is generally used to measure electrical signals and/or stimulate cells of the body. This connection is usually an electrode lead of the type described above. Currently, electrical signals are transmitted between the implant and the electrode contacts (e.g., tip, rings, HV shock helixes, sensors, etc.) using materials having good electrical conductivity.

If a system comprised of an implant and an electrode is exposed to strong interference fields (e.g., EMI, MRI), unwanted consequences can occur, especially a heating-up of parts of the system or electrical malfunctions (i.e., resets). The heating can result in damage to bodily tissue or organs if the heated parts have direct contact with such tissue. This is the case with the electrode tip, in particular.

The unwanted malfunction is generally caused by the interaction of the field with the elongate lead structure of the electrode: The electrode functions as an antenna and receives energy from the surrounding fields. The antenna can dissipate this energy on the leads, which are used for therapeutic purposes, distally into the tissue via the electrode contacts (e.g., tip, ring, etc.), or proximally into the implant. Similar problems occur with other elongate conductive structures, the proximal end of which is not necessarily connected to an implant (i.e., catheters, temporary electrodes, etc.).

Shielded electrodes are known. The shielding of the electrode mainly counteracts electrical fields that are coupled in from the outside. In addition, these shieldings provide only a particular shielding strength and are stable over the long term. A compromise must therefore be found between increasing the diameter of the electrode—which would have a corresponding effect on the costs and handling of the electrode—and a diminished shielding effect. Due to the high requirements on biocompatibility and biostability, materials that have proven useful in terms of the shielding effect thereof, e.g., soft magnetic nickel-iron alloys, cannot be used.

To prevent interferences by magnetic alternating fields and, in particular, in magnetic resonance apparatuses (MRI), especially to limit the heating of the electrode tip in fields of this type, it was proposed in U.S. Publication No. 2008/0243218 to provide a protective conductor in an electrode lead that turns back on itself in the longitudinal direction. This "billabong" principle utilizes mutual inductances to diminish induced currents. In this case, however, the three-layered helical winding is likewise expected to increase the diameter of the electrode.

The present inventive disclosure is directed toward overcoming one or more of the above-identified problems.

SUMMARY

A problem addressed by the present inventive disclosure is that of providing an improved implantable lead of the type described initially that has improved properties in strong external alternating magnetic fields and has a simple design, thereby enabling it to be produced at low cost.

This problem is solved by an implantable lead having the features of the independent claim(s). Further advantageous developments of the present inventive disclosure are the subject matter of the dependent claims.

The present invention is based on the idea of utilizing a plurality of separate, individually insulated conductors (especially those having a lead structure which is present per se) to implement the aforementioned billabong principle, instead of "folding" one continuous conductor. It is also based on the idea of electrically interconnecting the separate conductors at a point which then functions as a reversal point in the lead. It is understood that, to prevent irregular signal transmissions, at least one of the separate conductors is interrupted and/or must not be connected on at least one of the ends thereof.

The arteries that remain when the billabong circuit is implemented have a damping effect, even without resistive contact, or they are still contacted in nodes, and extend in parallel with an open end and function as an energy sink (i.e., Lecher lead) due to mismatch.

Without utilizing the billabong principle, the following variants also result:

1. Other conductors are connected in parallel, incrementally, with axial separation, to the continuous therapeutic conductor, and are open on the end thereof and axially reduce the wave impedance of the lead.

2. Other conductors are connected in parallel with the therapeutic conductor, which are shut off toward the electrode head. The wave impedance in the direction of the head is thereby increased. The energy that is coupled in is reflected.

In expedient embodiments that are characterized largely by the technological details of the manufacture of diverse medical leads, the separate conductors are securely interconnected by a soldered connection, a welded connection, or a bonded connection using conductive adhesive. However, other connection methods are also contemplated.

In another embodiment, which is also novel from a technological perspective, the separate conductors are securely interconnected by, for example, crimping, in particular, using a crimp clamp. In a suitable embodiment, the latter connection method is particularly technologically simple and therefore low-cost. The location of the connection point can be selected in a particularly flexible manner using a crimp connection, in particular, although a constant crimping process can be used. Supply leads can be produced, for instance, that can be adapted individually to the prevailing conditions and are thereby optimized in terms of the heating thereof, for example.

The connection points designed in said manner are then protected using an insulating material in a suitable form. They can be bonded, cast, extruded, or enclosed.

To link an additional functionality to the embodiments of the present invention, other embodiments are designed such that one or more electrical components, in particular, a resistor, a capacitor, an inductor, a filter component, an integrated circuit, a sensor component, or an actuator, are provided in the interchange point, or reversal point. One example of an actuator is an implantable drug pump which is controlled using the supply lead according to the present invention. Another example relates to mechanical devices on the electrode end for affixation of the electrode, which are operated via the cable. The fundamental electrical properties of the lead can therefore be optimized with respect to certain conditions of use, or the lead can improve the scope of functionality or the functioning of an electronic medical device attached thereto.

In structural variants of the present invention, the lead pole comprises n≥2 separate and individually insulated conductors, of which two or more are electrically interconnected at each interchange point, or reversal point, such that the lead pole comprises one to (n−1) reversal points. This can be designed, in particular, such that the, or an, electrode pole comprises separate and individually insulated conductors which extend along the axis of the lead in parallel, or about the axis in the manner of a helix, wherein one or two reversal points are formed.

The present invention can be used, for example, directly in the widespread multipolar electrode leads such that it comprises a plurality of lead poles, each of which has at least two separate and individually insulated conductors and at least one interchange point, or reversal point.

In an embodiment that is adapted to common types of electrode leads, the separate conductors of the lead pole are elongated conductors that extend parallel to one another and are woven in the manner of a rope, in particular. An embodiment that is adapted to another common type of electrode lead is characterized in that the separate conductors of the, or a, lead pole are designed as conductor helixes which, in particular, are interwoven or are disposed coaxially to a longitudinal axis of the lead. In another embodiment, one of the separate conductors of the, or an, electrode pole is at a potential that is independent of electrode potentials and has a shielding effect, in particular.

In addition to device-related aspects, the present invention also has manufacturing-related aspects which are expressed in a method having the features of the independent method claim(s). The present invention is characterized in that separate and individually insulated conductors, which are provided initially, are stripped locally and specifically, and are electrically interconnected at the stripped points to form interchange points, or reversal points, and the resulting lead poles are then embedded in the lead body.

In a method-related embodiment, laser processing or resistance welding is used to destroy the insulation and electrically connect the separate conductors to form the interchange point, or reversal point. In an alternative embodiment that is technologically particularly simple and low-cost, crimping is used to destroy the insulation and electrically connect the conductors to form the reversal point, in particular, using a crimp clamp.

Another embodiment is advantageous with respect to the aspect of technological simplicity and the use of established methods of plastics processing and, therefore, with respect to low costs, according to which the lead body is formed by coating the electrode pole, in particular, the integrated coating of a plurality of electrode poles, or extruding a plastic body around the electrode pole or electrode poles.

Other aspects of embodiments of the present invention are the following, which are in no way meant to be limiting:
1. The reversal points are designed as electrical short-circuit points.
2. Depending on the electrode pole, at least four mutually electrically insulated conductors are disposed along the symmetry axis of the lead body, and which are arranged, for example, in the shape of an "x" or a star in the cross-sectional area thereof, each comprising at least one interchange point, or reversal point, along the lead body.
3. At least four individually insulated conductors, which extend helically about a core along the symmetry axis of the lead body, are provided for each electrode pole, and are arranged, for example, in the shape of an "x" or a star in the cross-sectional area thereof, each comprising at least 1 reversal point along the lead body, and two or more conductors are electrically connected in parallel.
4. At least four individually insulated conductors, which extend helically about a core along the symmetry axis of the lead body, are provided for each electrode pole, and are arranged, for example, in the shape of an "x" or a star in the cross-sectional area thereof, each comprising at least one interchange point, or reversal point, along the lead body and, in each case, one of the electrically insulated conductors lies on a potential that is independent of the electrode potential.
5. The two to nine conductors are combined in one conductor complex, and are insulated from each other.
6. The conductors in one conductor complex are twisted.
7. There is at least one interchange point or reversal point between at least two conductors in one conductor complex.
8. There is at least one change in position between at least two conductors in one conductor complex.
9. One electrical resistor is located at the reversal point, or the change in position point.
10. One electrical capacitor is located at the reversal point, or the change in position point.
11. One electrical inductor is located at the reversal point, or the change in position point.
12. One or more electromechanical elements (filters) are located at the reversal point, or the change in position point.
13. One or more electrical circuits are located at the reversal point, or the change in position point.
14. A combination of the aforementioned electrical elements is located at the reversal point, or the change in position point.
15. One or more sensors are located at the reversal point, or the change in position point.
16. At least two of the conductors in one conductor complex are partially exposed by a laser.
17. At least one of the conductors in one conductor complex is severed by a laser.
18. At least two of the conductors in one conductor complex are welded together by a laser.
19. At least two of the conductors in one conductor complex are welded together by a resistance welding device.
20. At least two of the conductors in one conductor complex are soldered together.
21. At least two of the conductors in one conductor complex are interconnected by a crimp clamp.
22. Reversal points and redirection points represent a lead principle.
23. The conductors in one conductor complex are twisted.
24. The conductor complex is guided parallel to the axis in the lead body.
25. The conductor complex is guided helically about the axis in the lead body.
26. The conductor complex extends in the lead body in a helical shape with varying slope (including the parallel course).

27. The conductor complex extends in the lead body in a helical shape with a reversal of the slope of the helix.
28. Another insulated conductor can extend in the core. In one form, said conductor can be equipped with a lumen. In another form, it can also be designed to be rotatable or displaceable in order to transfer forces or moments. In a further form, it can be designed as an optical fiber.

Various other objects, aspects and advantages of the present inventive disclosure can be obtained from a study of the specification, the drawings, and the appended claims.

DESCRIPTION OF DRAWINGS

Advantages and useful features of the present inventive disclosure also result from the descriptive of embodiments and examples that follow, with reference to the Figures. They show.

DETAILED DESCRIPTION

Figure 1:
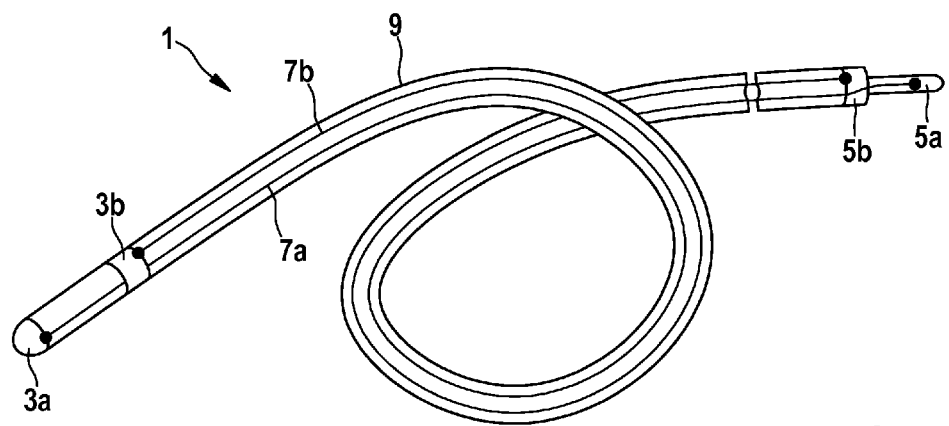
FIG. 1 shows a schematic representation of a conventional implantable electrode lead.

In the description of the Figures that follow, similar reference numerals are used for identical or identically-acting parts or sections, and previous descriptions are not repeated for subsequent Figures provided they refer to such parts and no special circumstances exist.

FIG. 1 is a schematic depiction of a bipolar electrode lead 1, on the distal end of which a tip electrode 3a and a ring electrode 3b are disposed. Two corresponding electrode contacts 5a and 5b are provided on the proximal end thereof, being connected to the respective associated electrode by a first and a second supply lead 7a and 7b. The electrodes, electrode contacts, and supply leads are accommodated on or in a lead body 9, which typically comprises multiple layers.

Figure 2:
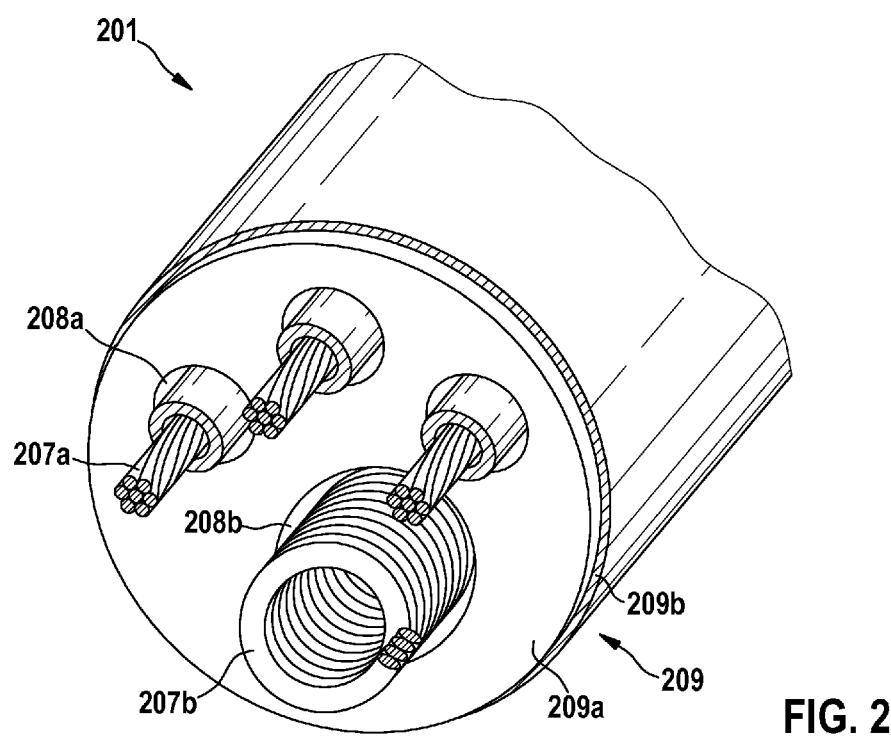
FIG. 2 shows, in a perspective sectional view, an example of a highly developed electrode lead comprising a plurality of supply leads accommodated in one lead body.

FIG. 2 shows, in a perspective sectional view having various cutting planes, a modern electrode lead 201, in the case of which three lumina 208a having a smaller diameter and an additional lumen 208b having a larger diameter are provided in an inner tube 209a which is the core of a supply lead body 209. Each of the smaller lumina 208a contains an electrode supply lead 207a having a rope structure which is provided with an insulating jacket comprised of, e.g., PTFE, ETFE or PI, and which is not labeled separately. A supply lead coil 207b, which can accommodate a guide wire during implantation to reinforce the electrode lead, extends in the larger lumen 208b. To improve the sliding and wear properties of lead body 209, it is provided with an outer shell 209b which positively influences these properties.

Figure 3:
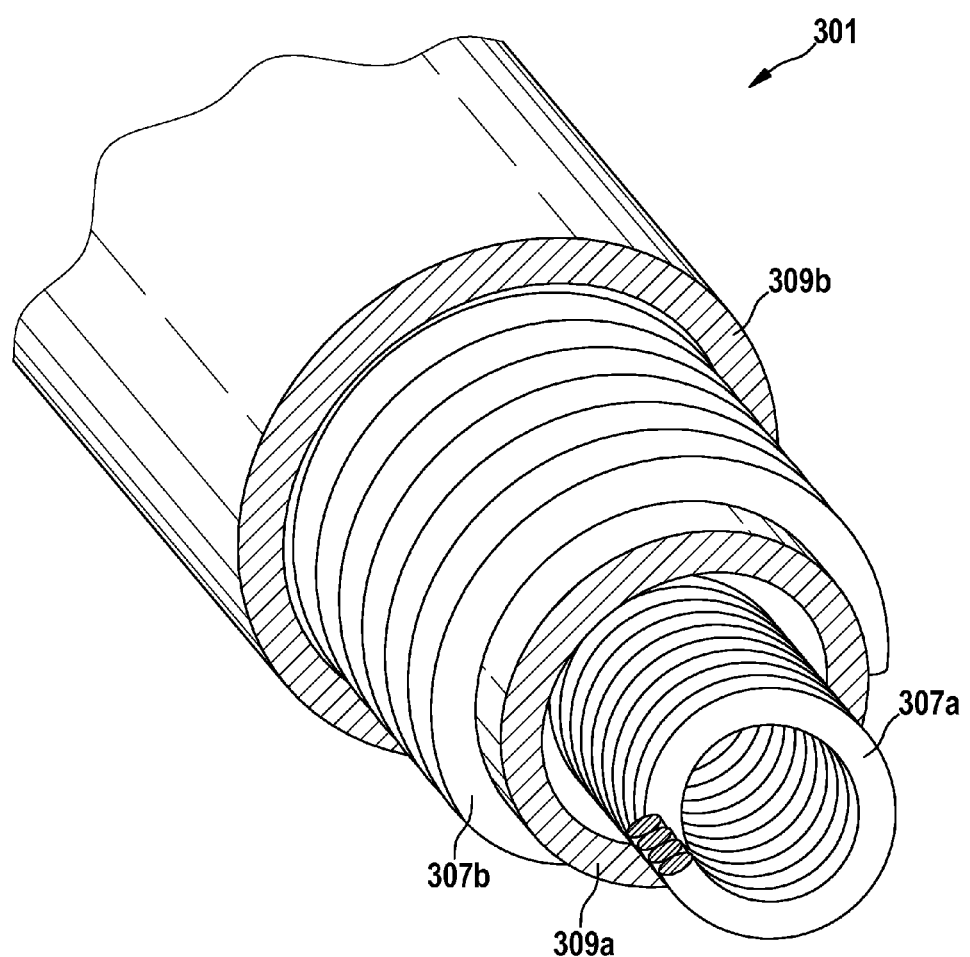
FIG. 3 shows, in a perspective sectional view, another highly developed electrode lead comprising a plurality of supply leads in a coaxial arrangement.

FIG. 3 shows a further embodiment of an implantable electrode lead, in the case of which an inner coil 307a, which comprises a plurality of wound individual wires, is disposed, as the first electrode supply lead (or the first group of electrode supply leads), coaxially to an outer coil 307b, which likewise comprises a plurality of wound individual wires (and which can likewise form a group of electrode supply leads). A silicone tube 309a is provided between the inner coil and the outer coil, and the outer coil is enclosed by a further insulating tube 309b which can likewise be comprised of silicone or a polyurethane or a copolymer, for example. A combination of a plurality of tubes can also be used here.

Figure 4A:
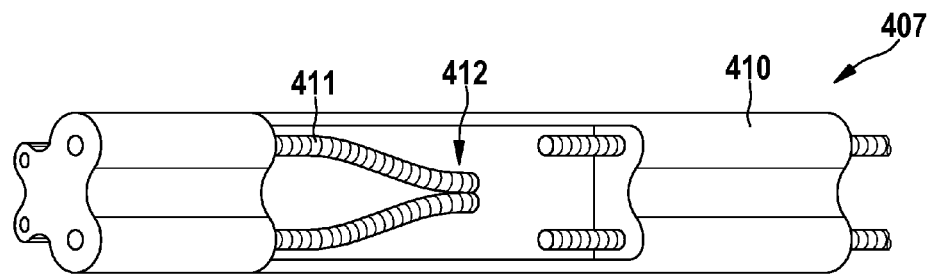
FIGS. 4A-4C show schematic depictions of embodiments of the present invention, in partial perspective sectional views.

FIG. 4A shows a supply lead 407 which can be embedded in a lead body (not shown), and can then be a component of an electrode lead. Supply lead 407 has a four-pole design and therefore comprises four separate strands or conductors 411 which are embedded in a plastic supply lead body 410 and are woven in the manner of a rope. As shown in FIG. 4A, two of the strands or conductors 411 have been severed along the course of the lead, and two ends which have been exposed as a result are interconnected in a conductive manner at a connection point 412 by, for example, welding, soldering, or conductive bonding.

If an electrical signal is applied from one end of supply lead 407 into one of the two interconnected conductors 411, and a corresponding signal is tapped at the other of the two interconnected conductors, then connection point 412 functions as a reversal point of a continuous lead course created by the electrical connection of the two conductors. Said reversal point makes it possible to achieve an effect which corresponds to the billabong principle and is based on the mutual inductance of conductor sections through which current flows in opposite directions, and which can be used to reduce the influence of external magnetic fields on the electrode lead structure.

Figure 4B:
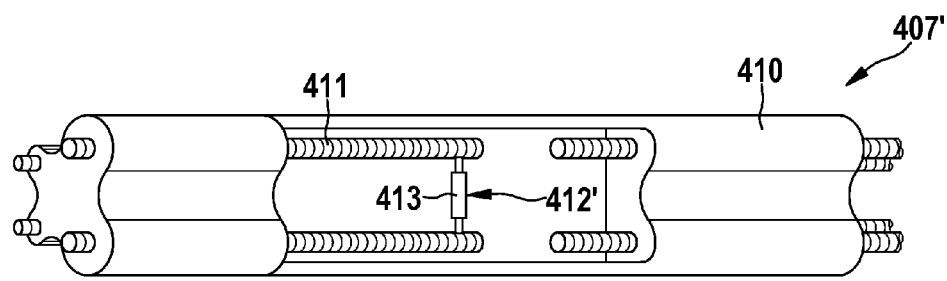

FIG. 4B shows another supply lead 407' which is a modified embodiment of the supply lead which is shown in FIG. 4A and is described above. In this case as well, at least two of the strands or conductors 411 extending in supply lead body 410 have been severed along the course of the particular lead, and have been electrically interconnected at a connection point (reversal point) 412'. In this case, however, an electrical or electronic component 413 is incorporated in said electrical connection, and can be an ohmic resistor, an inductor, a capacitor, or a filter element, for instance. It is also possible to provide a sensor component at the reversal point, which may be advantageous in terms of special functions of devices that are connected via the electrode lead.

Figure 4C:
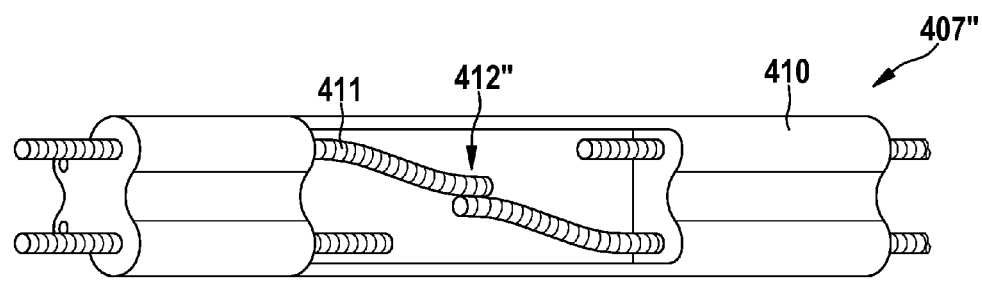

FIG. 4C shows, as another variant, a supply lead 407'', in which two strands or conductors 411 have been severed along the course of the particular lead, and have been electrically interconnected at a connection point 412".

In this case, however, the connection point is not a reversal point, but rather results in a change of position in the course of the lead (the beginning of the lead compared to the end of the lead).

The change of position changes the distance between the conductors and therefore adjusts the wave impedances that result in mismatches that convert the energy in the line instead of carrying it to the tip. According to the concept of the present invention, this distance can be adjusted very easily using design measures and can even be varied since conductors having different distances can be selected in one conductor bundle. It therefore determines the extent of the coupling of conductors extending in parallel, and therefore the effect of the damping. It is therefore possible to adjust the electrode to various requirements, such as, for example, 1.5-tesla or 3-tesla devices.

Figure 5:
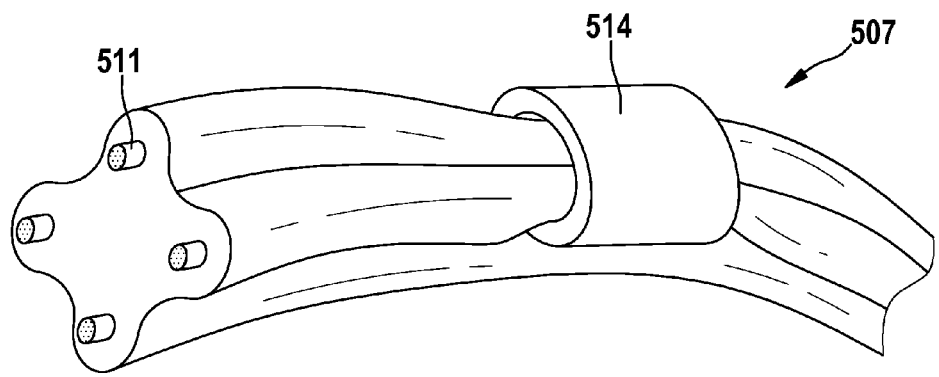
FIG. 5 shows a perspective view of another embodiment of the present invention.

FIG. 5 shows, using the example of a supply lead 507 of the type depicted in FIGS. 4A and 4B, a sketch of a possible embodiment of the simultaneous interruption of the course of the lead of two strands, or conductors, 511 and the mutual connection thereof at a reversal point. A crimp clamp 510 is used for this purpose, which is pressed over a portion of the circumference of supply lead 507 such that the lead interruption and mutual electrical connection of adjacent conductors 511 is brought about by the mechanical effect of clamp 514 which has a suitable geometric configuration around the inner circumference thereof.

Figure 6:
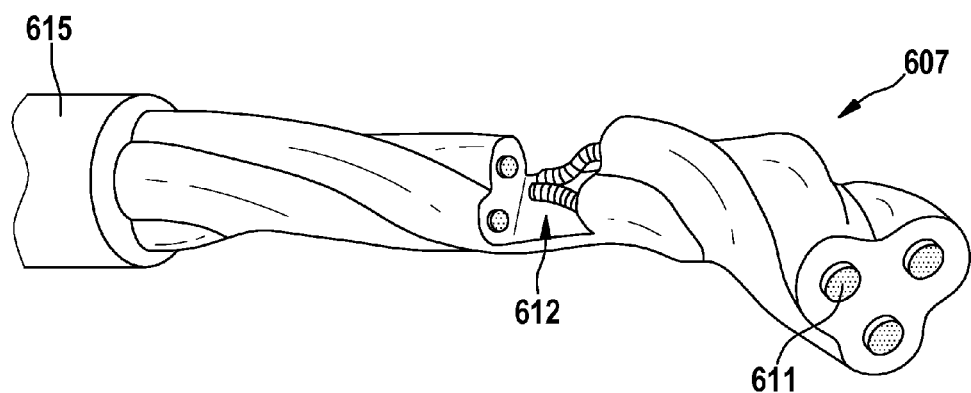
FIG. 6 shows a perspective view of a variant of the embodiment shown in FIG. 4A.

FIG. 6 shows, as another modification of the embodiment of the present invention depicted in FIG. 4A, a three-pole supply lead 607 having three strands, or conductors, 611, two of which are electrically interconnected at a connection and reversal point 612.

An insulating encapsulation of reversal point 612 and the "blind" ends of severed adjacent conductor 611 opposite thereto is accomplished using an extruded insulating shell 615 which is shown only partially in the left part of FIG. 6, but which extends along the entire length of finished supply lead.

Figure 7:
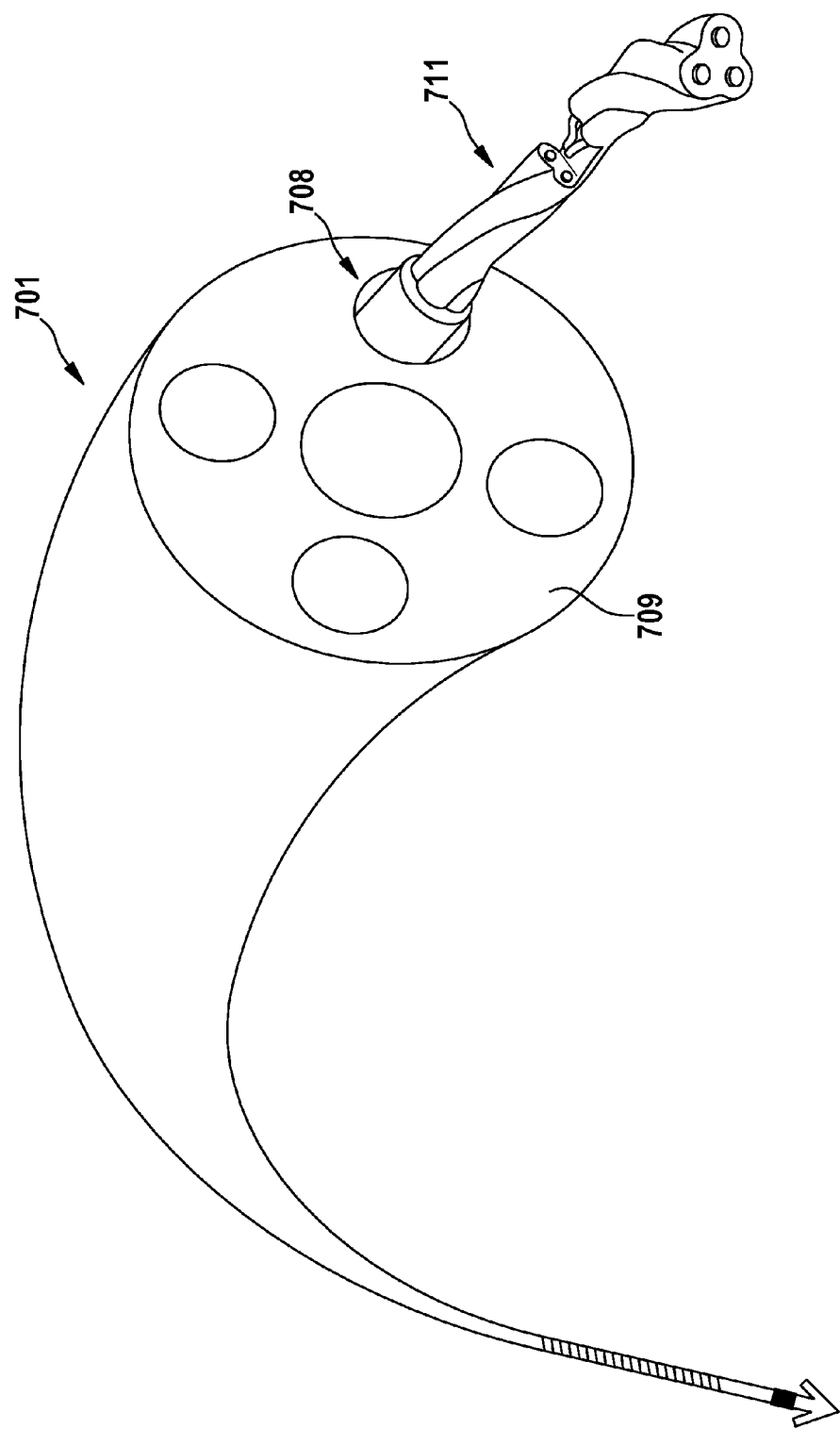
FIG. 7 shows a perspective view to illustrate the placement of the conductor complex—which is depicted in FIG. 6—in a lead body.

FIG. 7 shows how supply lead 711, which is protected by extruded tube 615 and is finished, is placed in one of the smaller lumina 708 of an electrode lead body 709 of an electrode lead 701.

Figure 8:
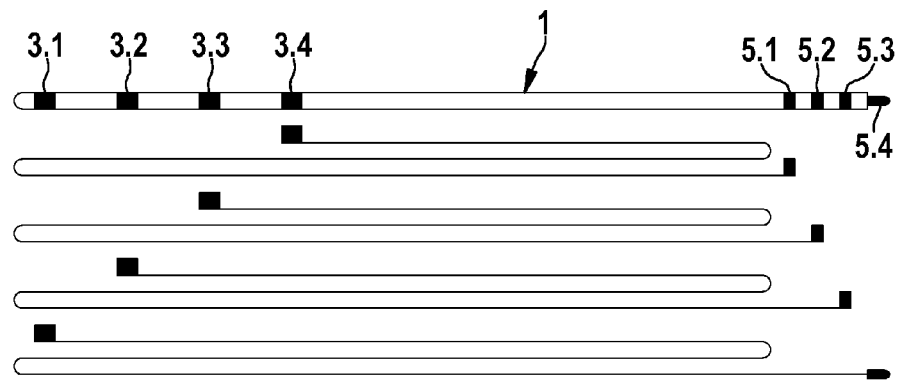
FIG. 8 shows a schematic depiction of a four-pole electrode lead in a first embodiment according to the present invention.
Figure 9:
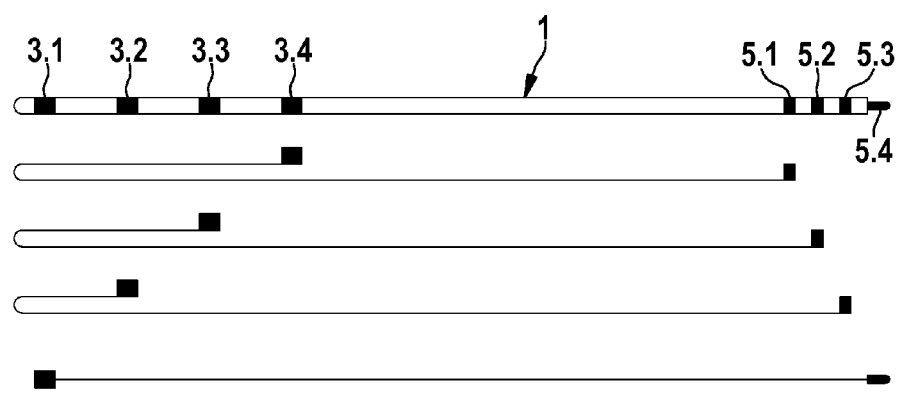
FIG. 9 shows a schematic depiction of a four-pole electrode lead in a second embodiment according to the present invention.
Figure 10:
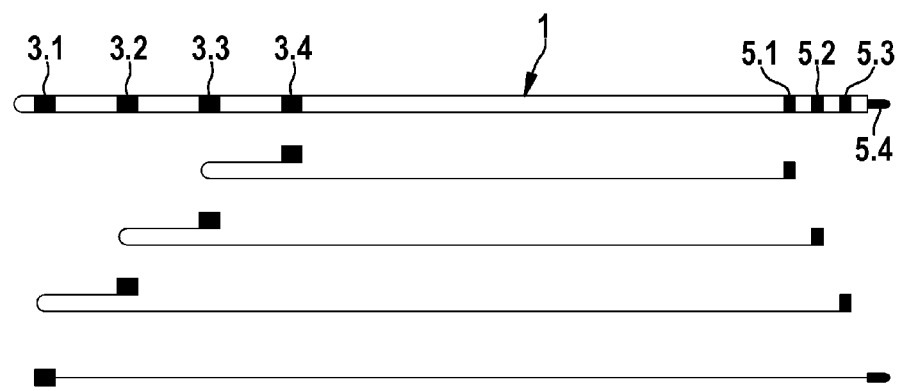
FIG. 10 shows a schematic depiction of a four-pole electrode lead in a third embodiment according to the present invention.

Different variants of electrode contacts 5.1 to 5.4 of a four-pole electrode lead 1 with electrodes 3.1 to 3.4 thereof disposed in the distal region are depicted schematically in FIGS. 8-10. In the variant shown in FIG. 8, each of the lead poles (which are not labeled separately) comprises two reversal points which are created according to the present invention by creating an electrical connection between adjacent strands or conductors extending in the lead body. In the embodiment shown in FIG. 9, three of the electrode poles each comprises a reversal point in the course of the lead thereof, while the fourth (between electrode connector 5.4 and electrode 3.1) does not have a reversal point. The connection between electrode connectors and electrodes in the variant shown in FIG. 10 has a similar design; in that case the conductor sections between the reversal point and the particular electrode in the distal section of the electrode lead have the same length in the three lead poles provided with a reversal point.

Figure 11A:
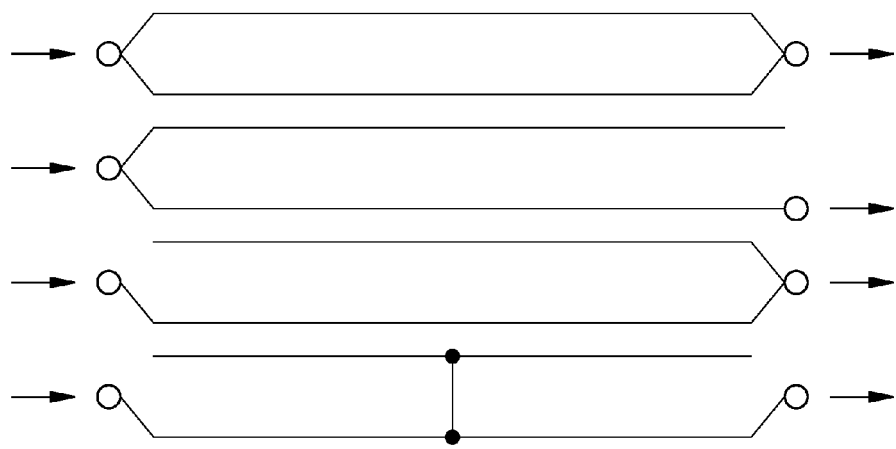
FIGS. 11A-11B show schematic depictions of variant connections which can be implemented according to the present invention in a two-pole supply lead.
Figure 11B:
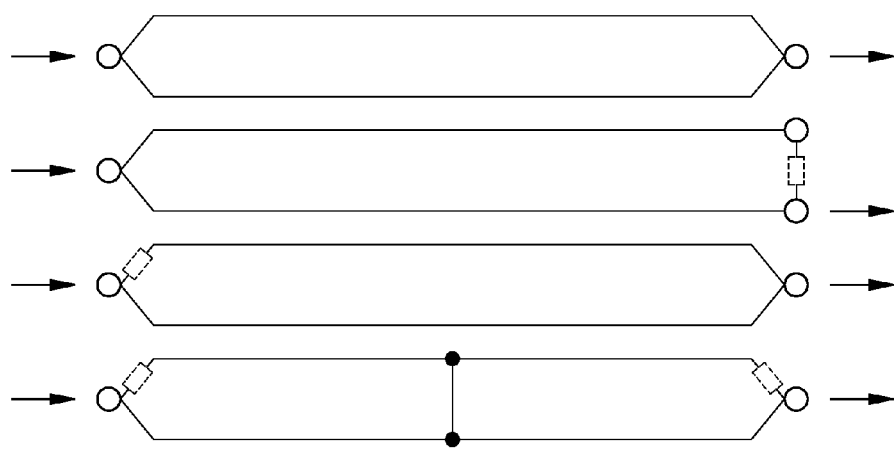

FIGS. 11A and 11B show schematic illustrations of variant connections having a two-pole line, in fact, with each being designed as a Lecher lead they are easily created using the design according to the present invention, and the effect of which in the MRT is damping due to mismatching.

Figure 12A:
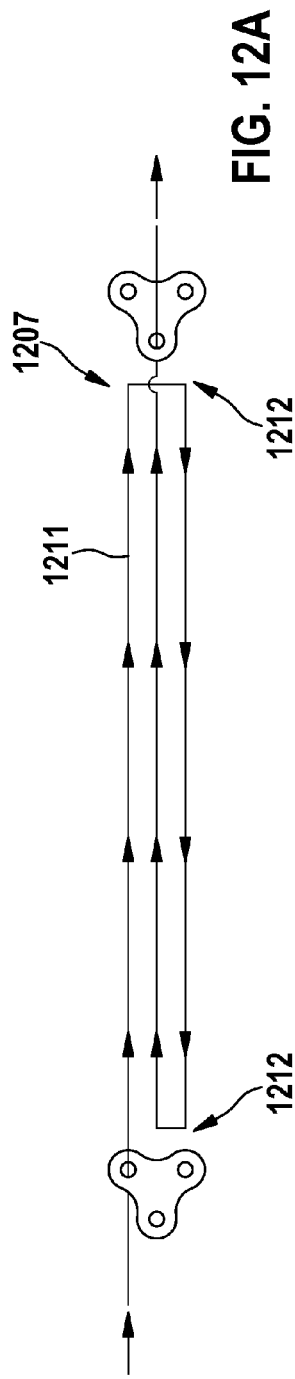
FIGS. 12A-12B show schematic depictions of variant connections which can be implemented according to the present invention in a three-pole supply lead.
Figure 12B:
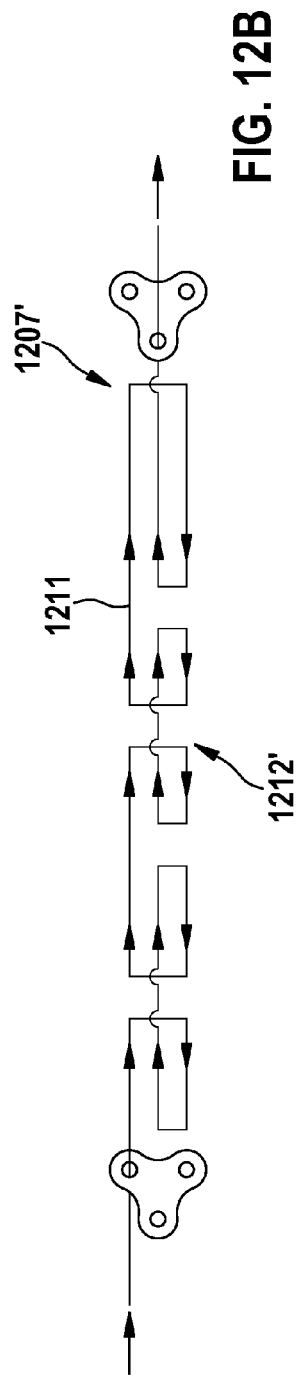

FIGS. 12A and 12B show two variants of the lead extension with a three-pole lead complex (of a supply lead) 1207. All three separate conductors 1211 of supply lead 1207 or 1207' are incorporated in a signal-carrying lead extension. The signal is applied in one end of the supply lead in the strand or conductor located at the top in the figures, and is tapped at the other end at the middle strand or conductor. Lead 1207' shown in FIG. 12A comprises two reversal points 1212 along the lead extension thereof, which are located close to the ends of the strands or conductor, while in the embodiment depicted in FIG. 12B, a plurality of connection and reversal points 1212' are created along the longitudinal extension of the conductor in each case, and the direction of current flow is reversed multiple times.

Overall, the supply lead can perform the function of a conventional conductor rope. In variants of both embodiments, the lead lengths between the reversal points can be varied and, possibly, the reversal points can be placed at varying distances (in order to obtain conductor sections of unequal length and different directions of current flow).

Figure 13:
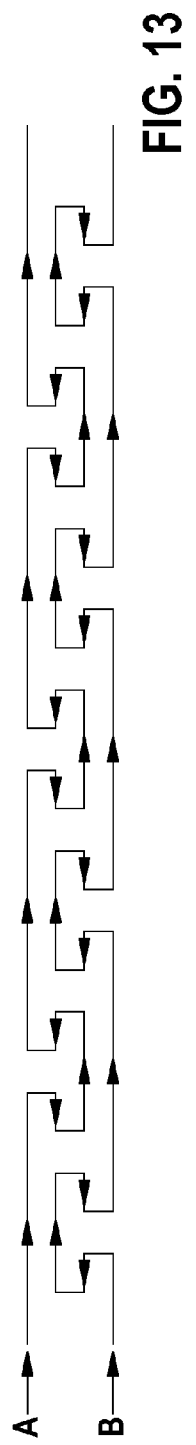
FIG. 13 shows a schematic depiction of a variant connection which can be implemented according to the present invention in a four-pole supply lead.

FIG. 13 is a schematic depiction of a current flow, which can be achieved in a four-pole supply lead (which is not depicted), in the case of which the four leads are used to obtain two electrical connections, and a plurality of reversal points are provided in each case. The four leads, which are used in pairs, can be used separately, e.g., for a supply lead and a terminal lead, or they can be connected in parallel. A special embodiment can comprise a twisting of the supply lead complex, and the supply lead can be installed in the electrode lead in a helical form.

The embodiments of the present invention are not limited to the above-described examples and emphasized aspects but, rather, are possible in a large number of modifications that lie within the scope of handling by a person skilled in the art.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof.

Additionally, the disclosure of a range of values is a disclosure of every numerical value within that range.

We claim:

1. An implantable medical lead for transmitting electrical impulses to excitable bodily tissue and/or electrical signals tapped at bodily tissue to a detection and control unit, comprising
   a distal electrode element;
   a proximal electrode connector element; and
   a lead pole which connects the distal electrode element to the proximal electrode connector element and extends in the lead body,
   wherein the lead pole comprises at least two separate and individually insulated conductors which are electrically interconnected or coupled at least at one point which functions as an interchange point or reversal point in the lead extension from the proximal electrode connector element to the distal electrode element, and
   wherein at least one of the separate conductors close to the interchange or reversal point is not connected at one end.

2. The lead according to claim 1, wherein the distal electrode element comprises a distal electrode, a distal sensor, or an actuator.

3. The lead according to claim 1, wherein the proximal electrode connector element comprises a proximal electrode connector or sensor/actuator connector.

4. The lead according to claim 1, wherein the separate conductors are securely interconnected by a soldered connection, welded connection, or bonded connection using conductive adhesive.

5. The lead according to claim 1, wherein the separate conductors are securely interconnected by crimping.

6. The lead according to claim 5, wherein the crimping is done using a crimp clamp.

7. The lead according to claim 1, wherein at least one electrical component includes a resistor, a capacitor, an inductor, a semiconductor element, a filter component, an electronic simulation of these elements, a sensor component, or a combination of components in an array or a circuit provided at the at least one interchange point or reversal point.

8. The lead according to claim 1, wherein the lead pole comprises n>2 separate and individually insulated conductors, of which two are electrically interconnected at each reversal point such that the lead pole comprises one to (n−1) reversal points.

9. The lead according to claim 1, further comprising a plurality of lead poles, each of which comprises at least two separate and individually insulated conductors and at least one interchange point or reversal point.

10. The lead according to claim 1, wherein the separate conductors of the lead pole are conductors that extend parallel to one another and are woven in the manner of a rope.

11. The lead according to claim 1, wherein the separate conductors of the lead pole are designed as conductor helixes which are interwoven or are disposed coaxially to a longitudinal axis of the lead.

12. The lead according to claim 1, wherein one of the separate conductors of an electrode pole is at a potential that is independent of electrode potentials and has a shielding effect.

13. The lead according to claim 1, wherein the electrode pole comprises separate and individually insulated conductors which extend along the axis of the lead in parallel, or about the axis in the manner of a helix, wherein one or two reversal points are formed.

14. A method for manufacturing an implantable medical lead according to claim 1, comprising the step of:
providing a pair or a group of separate and individually insulated conductors that are suitable for the manufacture of an implantable medical lead, wherein the pair group of separate conductors electrically connects a distal electrode element to a proximal electrode connector element;
locally destroying the insulation of the conductor such that an uninsulated conductor section of each of two conductors are located close to one another;
electrically connecting the two conductors to the uninsulated lead sections located close to one another to form the interchange point or reversal point; and
embedding the pair or group of separate conductors, which have been prepared as described above, as a lead pole in the lead body, and applying the electrode or the sensor to the distal end and the electrode connector or sensor connector to the proximal end of the electrode pole.

15. The method according to claim 14, wherein laser processing or resistance welding is used to destroy the insulation and electrically connect the separate conductors to form the interchange point or reversal point.

16. The method according to claim 14, wherein crimping is used to destroy the insulation and electrically connect the separate conductors to form the interchange point or reversal point.

17. The method according to claim 16, wherein the crimping is done using a crimp clamp.

18. The method according to claim 14, wherein the lead body is formed by coating the electrode pole of electrode poles, or extruding a plastic body around the electrode pole or electrode poles.

19. The method according to claim 14, wherein the lead body is formed by the integrated coating of a plurality of electrode poles.

* * * * *